United States Patent [19]

Brundin

[11] 4,365,621

[45] Dec. 28, 1982

[54] DEVICE FOR MEMBERS FOR CLOSING BODY PASSAGES

[75] Inventor: Jan-Olof Brundin, Lindingö, Sweden

[73] Assignee: AB Medline, Stockholm, Sweden

[21] Appl. No.: 227,068

[22] PCT Filed: May 5, 1980

[86] PCT No.: PCT/SE80/00130

§ 371 Date: Jan. 4, 1981

§ 102(e) Date: Dec. 23, 1980

[87] PCT Pub. No.: WO80/02369

PCT Pub. Date: Nov. 13, 1980

[30] Foreign Application Priority Data

May 4, 1979 [SE] Sweden ............................ 7903886-5

[51] Int. Cl.$^3$ ............................................ A61M 31/00
[52] U.S. Cl. ................................. 128/1 R; 128/334 R; 128/130
[58] Field of Search ............... 128/130, 1 R, 335, 270, 128/79

[56] References Cited

U.S. PATENT DOCUMENTS

| 2,616,424 | 11/1952 | Brown et al. ...................... 128/264 |
| 3,687,129 | 8/1972 | Nuwayser ........................... 128/1 R |
| 3,888,975 | 6/1975 | Ramwell ............................. 128/130 |
| 3,918,443 | 11/1975 | Vennard et al. .................... 128/130 |

FOREIGN PATENT DOCUMENTS 1,569,660  6/1980  United Kingdom .............. 128/1 R

*Primary Examiner*—V. Millin
*Assistant Examiner*—Nancy A. B. Swisher

[57] ABSTRACT

A device for temporarily or permanently closing body passages or cavities in humans and animals and including a member (2) of a material which swells at least 20% by absorbing body fluids and which is substantially inert to body fluids and surrounding tissues, the member (2) being dimensioned so as to be able to be introduced with clearance into the passage or cavity in its unswollen state but to take up the whole cross-section of the passage or cavity in the swollen state and then to be held by pressure against the surrounding walls of the passage or cavity. The device also comprises an element (7) with outer portions (8) which, in the unswollen state of the member, project out from its surface and which are made of a material with such suitable stiffness that the element with said outer portions (8) spreads out, in a yielding manner, towards the surrounding walls of the passage or cavity in such a manner that the element tends to lock the member in its inserted position by pressure against the wall, which ensures holding of the member before it has developed any direct pressure against the surrounding wall through its swelling.

10 Claims, 5 Drawing Figures

DEVICE FOR MEMBERS FOR CLOSING BODY PASSAGES

TECHNICAL FIELD

The present invention relates to a device for the temporary or permanent closing of body passages or cavities in humans and animals and comprising a member of a material which swells at least 20% by absorbing body fluids and which is substantially inert to body fluids and surrounding tissues, the member being dimensioned so as to be able to be introduced with clearance into the passage or the cavity in its unswollen state but to take up the whole cross-section of the passage or cavity in the swollen state and then to be held firmly by pressure against the surrounding wall of the passage or cavity.

BACKGROUND

The closing of body passages by means of members which can swell has previously been proposed. Such closing of passages and cavities in human or animal bodies may be justified for contraceptive reasons, in which case the oviducts or testicular ducts are closed, or for reasons of illness which require a blocking of a body passage.

The expansible member in question was previously made of fibrous substances which swell on absorbing body fluid, but later it was found that suitable materials are certain water-absorbing copolymerized plastics, so-called hydrogels. The closing is effected in that the expansible member is inserted in the unswollen state in the body passage in question. The shape and dimensions of the member are adapted so that it can easily be introduced into the passage. After introduction, it absorbs fluid from the surrounding tissues and swells. By this means, the passage is blocked as intended while at the same time the member obtains a firm hold therein. Nevertheless, the material should be substantially inert with respect to the body fluid and the surrounding tissues so that the member is retained intact and can be removed when it has served its purpose. As a result, the functioning of oviducts or testicular ducts can be restored, for example, after being blocked with a preventive aim.

TECHNICAL PROBLEM

It has been found, in practice, however, that there is a risk of the member being carried out of the passage, for example by muscular movement or being flushed away during the first period of time after insertion when it has not been able to absorb so much body fluid that it has assumed such a size that it presses against the surrounding walls of the passage. It is also conceivable in some connections that such an expansion of the cavity can occur, that the volume of the member is no longer sufficient and there is a risk of expulsion.

THE SOLUTION

According to the invention, the device also comprises elements with external portions which, in the unswollen state of the member, project out from its surface and which are made of a material with such suitable stiffness that the element with said external portions spreads out in a flexible manner towards the surrounding walls of the passage or cavity in such a manner that the element tends to lock the member in its inserted position by pressure against the wall.

ADVANTAGES

This affords a securing of the member before it has developed any direct pressure against the surrounding wall through its swelling and so eliminates said risk of expulsion. This is effected by simple means and in such a manner that the member, in its normal swollen state, performs its normal function of blocking the passage without any particular disadvantages.

BRIEF DESCRIPTION OF DRAWINGS

In the accompanying drawings, two forms of embodiment of a member constructed according to the invention are shown as well as four forms of embodiment of an element included in the device according to the invention.

BEST MODE OF CARRYING OUT THE INVENTION

Figure 1:
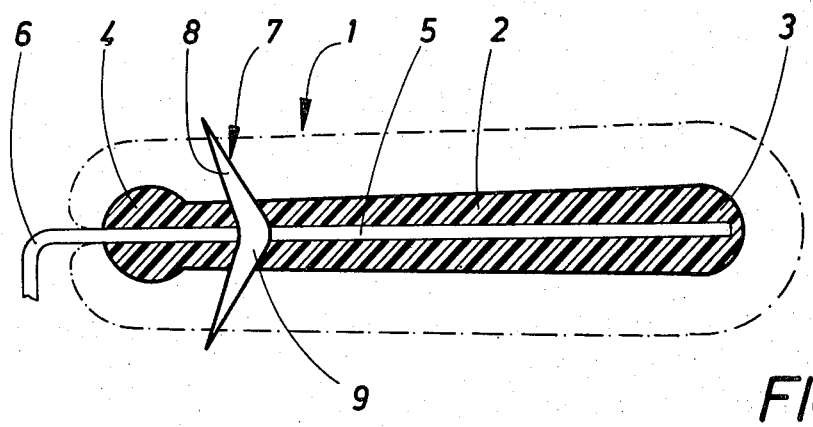
FIG. 1 shows, in longitudinal section, the member according to the first form of embodiment.

As stated, the device according to the invention consists of a member of a material which, when it is brought into contact with a body fluid, swells in volume by at least 20% measured as linear expansion. Apart from the swelling capacity, the member is substantially inert to body fluids and the surrounding tissues. The swelling of the member in contact with body fluid is preferably at least 40%, for example at least 80%. The swelling may vary between 20–300% linearly. The passage-shaped cavities in humans and animals which can be closed by the device according to the invention are, for example, blood vessels, ureters, testicular ducts and oviducts.

The geometrical shape of the member which is introduced into the passage-shaped cavity is not critical and the member may, for example, be substantially cylindrical, spherical, ovoid or hourglass-shaped. Nevertheless it may appropriately have a substantially cylindrical cross-section in the cross-section which corresponds to that of the passage-shaped cavity. This cross-section in the unswollen member is so much smaller than the cross-section of the passage-shaped cavity, that the member can be introduced into the cavity with clearance from its walls, as a result of which the introduction can take place with the minimum possible difficulty.

The present means is particularly suitable for use as a contraceptive means, in which case the member is introduced into the testicular duct or the oviduct. In the latter case, a thread may appropriately be secured to the member so that it can be taken out without operative intervention. This thread can be of a material which is proof against X-rays so that the position of the member can be checked. Alternatively, the member itself may be of a material which affords an X-ray contrast. The material in the member swells in contact with the body fluid at least 40%, preferably at least 80% and can swell up to 300%. Apart from this, the material should be substantially inert to body fluids and should not be harmful to and should not be resorbed by the body. A suitable group of materials are hydrogels. These materials swell by absorption of water out of the body fluids.

Suitable hydrogels are polymers and copolymers of the acrylic type, for example cross-linked polyacrylamide and polymers and copolymers of methacrylic acid esters with at least one hydroxy group in the side chain. Suitable monomers are 2-hydroxy-ethyl-methacrylate, in which case the ester groups can originate from diethylene glycol or triethylene glycol. 2,3-dihydroxypropylmethacrylate may also be used for example. Polyfunctional acrylates such as diesters or corresponding glycols, for example ethylene glycol bis-methacrylate, may be used as a cross-linking substance.

Another example of a material suitable for the member according to the invention is a copolymer of a hydrophilic monomer and a hydrophobic monomer. With this material, the capacity to absorb water and hence the swelling can be varied within wide limits by variation of the proportions between the hydrophilic and the hydrophobic monomers. Examples of the hydrophilic components are monomers in the group consisting of N-vinyl-pyrrolidones and vinyl pyridines and examples of the hydrophobic components are monomers in the group consisting of methylacrylate and methylmethacrylate. The polymerisation may appropriately be effected in that the raw material is exposed to electromagnetic radiation in the ultraviolet-gamma radiation range or by heating.

The member should be substantially resilient and only plastic to a very small extent. It may be stiff and/or hard in the unswollen (non-hydrated) state, but should soften on swelling. The member may contain means which makes it more dense to X-rays, for example barium or bismuth salts or metal powder (for example silver).

When used, the member is introduced into the passage-shaped cavity in the unswollen state and later swells in contact with body fluids so that the member, which on introduction can pass through the cavity, swells and is brought into satisfactory contact with the walls of the cavity. As a result of the pressure which is then exerted on the member from the walls, the resilient member is compressed while at the same time the resilient walls of the cavity may expand. As a result, the member fills in the whole cross-section of the cavity and prevents passage through the cavity, while at the same time the member is held firmly in position in the cavity. After insertion in an oviduct, for example, the passage of eggs down to the womb or of semen up through the oviduct to the unfertilized egg is prevented. If a testicular duct is closed, the passage out of semen is prevented and a good preventive protection is obtained. The inserted members can be removed again if desired by an operation or, as is the case on insertion in the oviduct, by pulling out to the uterus if the member is provded with a thread hanging down through which pulling can be effected.

Thus, in its inserted position, the member has a satisfactory anchoring in the body passage or the cavity into which it is introduced, after the material of the member has absorbed body fluid and swollen. This takes some time, however, and before this has happened, the member has clearance with respect to the surrounding tissue walls. As stated, in its unswollen state, the member is so much smaller than the cavity or passage that it can easily be introduced into the body cavity in question. If the member is to be introduced a long way into a body passage and has to pass a point which is narrower than the point where the member is to be placed, a considerable underdimensioning is necessary for the member. The idea behind the device is also that the member should have this smaller dimension on introduction but should assume the larger dimension which is required for secure holding and effective blocking of the passage after placing in the intended position.

The circumstances mean, however, that the member does not have any secure anchoring before the swelling has taken place and therefore a period of uncertainty occurs immediately after insertion, when, under unfavourable circumstances, the member may be displaced by flow of body fluid through the passage or movement in that which carries the inserted member. This uncertainty in operation is eliminated, however, by the present invention. This is effected as a result of the fact that the member is equipped with at least one element of a material with a suitable stiffness. This element comprises external parts which at least in the unswollen state of the member project out of the member so far that they come into contact with the walls of the surrounding cavity when the member is inserted in the intended manner. As a result, these projecting parts act as locking elements which spring and hold the member in its introduced position. These resilient elements may appropriately be made with a locking action so that they spring down in the direction of introduction but tend to spread out on a movement out of the passage.

Thus the projecting parts of the element serve as an anchoring only or mainly before the member has assumed its swollen state. They can therefore have such dimensions that they are mainly within the surface of the member when this has assumed its swollen state and is held by this. By this means, the projecting portions are prevented from pressing in to too great an extent into the surrounding body tissue in the continuous state, when the member has assumed its swollen state.

A device 1 according to the invention adapted for insertion in a woman's oviduct is shown in longitudinal section in FIG. 1. It is formed from an elongated, cylindrical (see FIG. 2) member 2 of said expansible material with an inner rounded end 3 and an outer spherical end 4. Included in the member 2 is a thread 5, preferably of nylon, which ends before the inner end 3 but extends out from the member 4 at the end 4 with a free portion 6.

Examples of suitable dimensions for the member 2 for the application described are a length apart from the free portion of the thread 6 of 11 mm and a maximum diameter of 1.6 mm. Alternatively, the member may have the shape of a drop with a diameter of about 0.8 mm in the unswollen state.

The thread 5 is preferably of polyamide fibre and is made at least partially opaque to X-rays.

Figure 2:
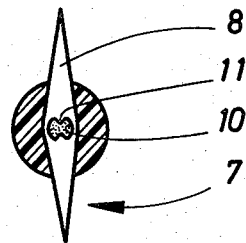
FIG. 2 shows the same member in cross-section.

One or more elements 7 for said anchoring of the member extend through this and comprise projecting portions 8 in the unswollen state of the member 2. The central portion 9, from which the external portions 8 originate, is inside the material of the member 2 even in its unswollen state and thus forms an anchoring for the element 7. In addition, the thread 5 extends through a hole 10 in the element 7, so that an exceptional mutual anchoring of the element 7 and the thread 5 is obtained in the material of the member 2. The holding together of the thread 5 and the element 7 is also an advantage in producing the device 1 since only one element needs to be inserted in the shaping tool and during the actual shaping, the parts in question can be held by holding the projecting portions 8 of the element 7, which project from the actual shaping space for the member 2. A satisfactory holding together between the element 7 and the thread 5 can be obtained if the hole 10 is provided, as indicated in FIG. 2, with turned-in parts 11 which project into the thread 5. An alternative securing is shown in FIG. 4 where the thread 5 is provided with knots 12 at each side of the element 7.

Figure 4:
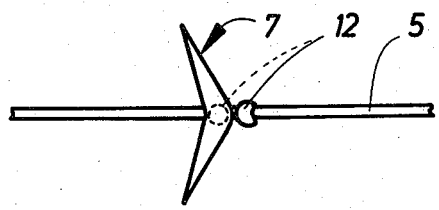
FIG. 4 shows an element included in the member in one form of embodiment.

In the embodiment of the element 7 shown in FIGS. 1, 2 and 4, its two halves at the sides of the hole 10 form triangular wings turned in towards one another. These may appropriately be at least somewhat concave at their side turned towards the other half, as indicated in FIG. 4. The shape and thickness can be adapted in extent to the material selected and the necessary resilient forces. The intention is that the measurement over the ends of the element 7 should be somewhat greater than the internal dimensions of the proposed body passage, so that the element 7 spreads out towards its walls but in a yielding manner so that the outer portions 8 can fold in if a narrower passage space is traversed during the introduction. As a result of the flexibility, an adaptation to different passage cross-sections is also obtained.

The material in the element 7 must be able to be tolerated by the body in which the device is inserted. Some semi-stiff, resilient plastics material such as acetal plastics or amide may appropriately be used.

Figure 3:
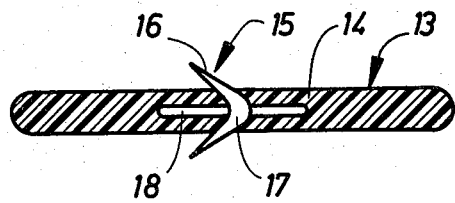
FIG. 3 shows the member according to the second form of embodiment, in longitudinal section.

FIG. 3 shows, in longitudinal section, a device 13 according to the second example of embodiment. This device is adapted to be inserted in the testicular duct and has its dimensions and its shape adapted to this purpose. An elongated, cylindrical shape is suitable with a length of 6 mm for example and a diameter of about 0.6 mm, which applies to the member made of expansible material in the unswollen state, which is designated by 14.

Insertion in the testicular duct cannot be effected from the outside but must be done by operative intervention, when the testicular duct is opened, after which the device can be pushed in and the testicular duct closed again. The unswollen state of the member 14 means that the member has smaller dimensions than the inner extent of the testicular duct so that the introduction is facilitated. After the introduction, the member 14 swells as described previously by absorbing body fluids. The removal of the device, if desired, is also effected by an operative intervention. It is therefore pointless to provide the device with any thread and in order that its position may be checked by means of X-rays, the material of the member 14 should be made at least partially dense to X-rays for example by including metals or metal salts therein. The device 13 also has an element 15 for anchoring in its unswollen state. Like the element 7, this comprises outer portions 16 turned towards one end of the member 14, which are flexible and can spread out towards the wall of the testicular duct. The outer portions and a central portion 17 embedded in the member 14 are made in one piece with a rod-shaped central portion 18 which affords anchoring in the member 14. The element 15 has very small dimensions because the member 14, as stated, has a diameter of less than 1 mm.

Figure 5:
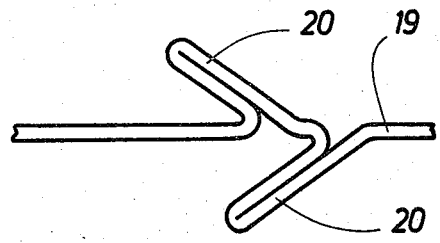
FIG. 5 shows the element in another form of embodiment.

FIG. 5 shows an alternative form of the anchoring device. In this case a thread 19 of polyamide fibres is used. This thread can be used in the same manner as the pulling-out thread 5 and then projects out of the expansible member. It may, however, also be so short that it only constitutes a holding portion like the portion 18. The projecting wings which are to form the outer portions are formed by loops 20 on the thread 19. These loops can be held together in the shape shown and may even be made stiff by heating, so that the material partially melts from the fibrous structure in the thread 19 to an amorphous structure. By using a thin thread, very small anchoring elements can be produced in this manner.

Thus, through the resilient wings of the anchoring element, an anchoring of the device is obtained during its unswollen state. As a result of the back-swept shape of the wings as shown, these can yield downwards during the introduction but tend to spread out if an attempt is made to withdraw the device. When the expansible member swells, the outer portions of the anchoring element disappear least partially in the member, as indicated in FIG. 1, where a chain line approximately shows the size of the member 2 after swelling. With a great swelling capacity and body tissues which can be forced aside, the cavity may expand so much that the anchoring element completely loses contact with the walls of the cavity, even if the outer tips of the element were in contact with the walls on introduction. In this manner any conceivable irritation through the tips of the element can be avoided in the continuous state.

The member 2 or 13 preferably consists of a hydrophilic monomer such as polyvinylpyrrolidon and a hydrophobic one such as acrylate or polyamide which has been secured to the thread or the element by means of copolymerisation (graft polymerisation). The swelling and the forces exerted through the absorption of water from body fluids can be varied by altering the proportions between the hydrophilic and the hydrophobic monomers. Three (3) parts of the hydrophilic monomer (vinylpyrrolidon) and one (1) part of the hydrophobic monomer (polyamide) form a copolymer with an expansion factor of 1.48 calculated linearly (swells 48% in water) with a water content of 66%; five (5) parts of the hydrophilic monomer and one (1) part of the hydrophobic monomer provide a copolymer with an expansion factor of 1.72 with a water content of 78%.

INDUSTRIAL APPLICABILITY

Despite the fact that the device according to the invention is described in the form of a contraceptive means, it is understood that other applications may occur, for example in the event of brain injury such as cerebral enlargement of the artery or for treatment of phlebectasis. In this case, the device is inserted in the vessel in question so as to shut this off completely. For such an application an hourglass shape of the device is preferred.

I claim:

1. A device for the temporary or permanent closing of a body passage or cavity in humans and animals, comprising: a member of a material which swells at least 20% when absorbing body fluids and which is substantially inert to body fluids and surrounding tissue, said member being dimensioned so as to be able to be introduced without any substantial pressure against the walls of the passage or cavity in the unswollen state of the member but to take up the whole cross-section of the passage or cavity in the swollen state and then to be held by pressure against the surrounding wall of the passage or cavity, at least one element incorporated in said device and having a number of external portions extending from a center portion of said element and provided with free ends, the element having its center portion and the innermost parts of the extending portions embedded in said member while the free ends of said portions extend outside the member at least in the unswollen state of the member, said portions being made of a material with such suitable stiffness that said portions spread out in a yielding manner towards the surrounding walls of the passage or cavity in such a manner that the portions tend to lock the member in its introduced position by pressure against the walls by means of said ends, with adaption to the passage or cavity, which ensures securing of the member even before it has developed any direct pressure against the surrounding walls due to its swelling.

2. A device as claimed in claim 1, wherein said external portions of the element are inclined and are so directed in the intended direction of introduction into the passage or cavity that the external portions tend, during said introduction to fold in towards said member but with forces in withdrawal direction tend to fold out from said member.

3. A device as claimed in claim 2, wherein said external portions are wing-like projections.

4. A device as claimed in claim 3, wherein said center portion of the element is formed by a first portion of a thread, which extends outside the member with another portion.

5. A device as claimed in claim 4, for closing the oviduct of a woman or a female animal, wherein said member has an elongated shape with a diameter of about 1-2 mm and including said first portion of the thread, to which there is secured an element of stiff material such as plastics and having at least two wing-like portions, the outer ends of which form said free ends.

6. A device as claimed in any one of claims 1 to 5, wherein the distance by which the element projects out from the surface of the member corresponds substantially to the distance by which the wall of the member from which the external portions of the element extend swells when absorbing body fluids, so that the element and its said external portions are substantially included in the member in its swollen state.

7. A device as claimed in claim 1, wherein the material of the member consists of a hydrogel.

8. A device as claimed in claim 7, wherein said hydrogel is of the acrylic type.

9. A device as claimed in claim 8, wherein said hydrogel is a copolymer of methacrylic acid esters with at least one hydroxy group in its side chain and with polyfunctional methacrylate.

10. A device as claimed in any one of claims 7, 8 or 9, wherein the hydrogel is a copolymer of at least one hydrophilic monomer and at least one hydrophobic monomer.

* * * * *